(12) United States Patent
Shimada et al.

(10) Patent No.: US 9,745,279 B2
(45) Date of Patent: Aug. 29, 2017

(54) SIRTUIN ACTIVATOR

(71) Applicants: TOKIWA PHYTOCHEMICAL CO., LTD., Sakura-shi, Chiba (JP); Masaki Aburada, Abiko-shi, Chiba (JP)

(72) Inventors: Tsutomu Shimada, Tokyo (JP); Jinwei Yang, Chiba (JP); Yuka Koike, Chiba (JP)

(73) Assignees: TOKIWA PHYTOCHEMICAL CO., LTD., Sakura-shi, Chiba (JP); Masaki Aburada, Abiko-shi, Chiba (JP)

(*) Notice: Subject to any disclaimer, the term of this patent is extended or adjusted under 35 U.S.C. 154(b) by 202 days.

(21) Appl. No.: 14/368,457

(22) PCT Filed: Dec. 27, 2012

(86) PCT No.: PCT/JP2012/084000
§ 371 (c)(1),
(2) Date: Jun. 24, 2014

(87) PCT Pub. No.: WO2013/100111
PCT Pub. Date: Jul. 4, 2013

(65) Prior Publication Data
US 2014/0348961 A1    Nov. 27, 2014

(30) Foreign Application Priority Data

Dec. 27, 2011 (JP) ................................. 2011-290691
Mar. 22, 2012 (JP) ................................. 2012-087902

(51) Int. Cl.

| | | |
|---|---|---|
| A61K 36/00 | (2006.01) |
| C07D 311/32 | (2006.01) |
| A61K 31/352 | (2006.01) |
| A23L 2/52 | (2006.01) |
| A61K 36/9068 | (2006.01) |
| A61K 8/49 | (2006.01) |
| A61Q 19/00 | (2006.01) |
| A61K 8/97 | (2017.01) |
| A23L 33/105 | (2016.01) |

(52) U.S. Cl.
CPC .............. *C07D 311/32* (2013.01); *A23L 2/52* (2013.01); *A23L 33/105* (2016.08); *A61K 8/498* (2013.01); *A61K 8/97* (2013.01); *A61K 31/352* (2013.01); *A61K 36/9068* (2013.01); *A61Q 19/00* (2013.01); *A23V 2002/00* (2013.01); *A61K 2236/00* (2013.01); *A61K 2800/10* (2013.01); *A61K 2800/78* (2013.01)

(58) Field of Classification Search
None
See application file for complete search history.

(56) References Cited

U.S. PATENT DOCUMENTS

| | | | |
|---|---|---|---|
| 2004/0214882 A1* | 10/2004 | Guthrie | ............... A61K 31/35 514/456 |
| 2006/0276416 A1 | 12/2006 | Sinclair et al. | |
| 2014/0148504 A1 | 5/2014 | Hwang et al. | |

FOREIGN PATENT DOCUMENTS

| | | | |
|---|---|---|---|
| CN | 101269061 A | * | 9/2008 |
| JP | 3010210 A | | 12/1999 |
| JP | 2003-192588 A | | 7/2003 |
| JP | 2004-083417 A | | 3/2004 |
| JP | 2005-206546 A | | 8/2005 |
| JP | 2008-528510 A | | 7/2008 |
| JP | 2009-51790 A | | 3/2009 |
| JP | 2009051790 A | * | 3/2009 |
| JP | 2009-67731 A | | 4/2009 |
| JP | 2010-209051 A | | 9/2010 |
| KR | 2011001359 A | * | 1/2011 |

(Continued)

OTHER PUBLICATIONS

Chaturapanich, Effects of Kaempferia parviflora extracts on reproductive parameters and spermatic blood flow in male rats. Reproduction (Cambridge, England), (Oct. 2008) vol. 136, No. 4, pp. 515-522.*

(Continued)

*Primary Examiner* — Qiuwen Mi
(74) *Attorney, Agent, or Firm* — Flynn, Thiel, Boutell & Tanis, P.C.

(57) ABSTRACT

The present invention provides a sirtuin activator with an active component composed of black ginger or a black ginger extract, which is easily obtainable, extremely safe, and eaten from old. The present invention further provides a sirtuin activator with an active component of polyalkoxy-flavonoid compound represented by general formula (I) and having a sirtuin activation effect that is 10 folds that of resveratrol or higher:

[Formula 1]

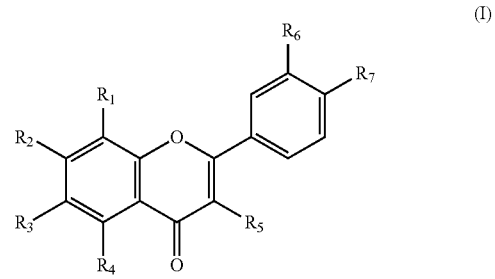

(I)

wherein, $R_1$ to $R_7$ are each independently a hydrogen atom, a hydroxyl group, or a C1 to C6 lower alkoxy group.

6 Claims, 4 Drawing Sheets

(56) References Cited

FOREIGN PATENT DOCUMENTS

| WO | WO 03/074065 A1 | 9/2003 |
| WO | WO 2006/079021 A2 | 7/2006 |
| WO | WO 2012/099449 A2 | 7/2012 |

OTHER PUBLICATIONS

Malakul et al, Effects of Kaempferia parviflora Wall. Ex Baker onendothelial dysfunction in streptozotocin-induced diabetic rats. Journal of ethnopharmacology, (Jan. 27, 2011) vol. 133, No. 2, pp. 371-377. Electronic Publication Date: Oct. 17, 2010.*

Wang et al, Anti-diabetic effects of pentamethylquercetin in neonatally streptozotocin-induced diabetic rats. European Journal of Pharmacology (2011), 668(1-2), 347-353.*

Akasa et al., "Antiobesity effects of *Kaempferia parviflora* in spontaneously obese type II diabetic mice," J. Nat. Med. (2011), vol. 65, pp. 73-80.

Donmez, G. and L. Guarente, "Aging and disease: connections to sirtuins," Aging Cell (2010), vol. 9, pp. 285-290.

English translation of International Preliminary Report on Patentability and Written Opinion issued Jul. 10, 2014, in PCT International Application No. PCT/JP2012/084000.

English translation of International Search Report mailed Apr. 2, 2013, in PCT International Application No. PCT/JP2012/084000.

Howitz et al., "Small Molecule Activators of sirutins extend *Saccharomyces cerevisiae* lifespan," Nature (2003), vol. 425, pp. 191-196.

Iwabu et al., "Adiponectin and AdipoR1 regulate PGC-1α and mitochondria by $Ca^{2+}$ and AMPK/SIRT1," Nature (Apr. 29, 2010), vol. 464, pp. 1313-1319.

Landry et al., "The silencing protein SIR2 and its homologs are NAD-dependent protein deacetylases," PNAS (May 23, 2000), vol. 97, No. 11, pp. 5807-5811.

Langley et al., "Human SIR2 deacetylates p53 and antagonizes PML/p53-induced cellular senesence," The EMBO Journal (2002), vol. 21, No. 10, pp. 2383-2396.

Nakao et al., "Xanthine Oxidase Inhibitory Activities and Crystal Structures of Methoxyflavones from *Kaempferia parvifloria* Rhizome," Bio. Pharm. Bull. (2011), vol. 34, No. 7, pp. 1143-1146.

Okuda, T. and K. Yokotsuka, "Trans-Resveratrol Concentration in Berry Skins and Wines from Grapes Grown in Japan," Am. J. Enol. Vitic. (1996), vol. 47, No. 1, pp. 93-99.

Sae-Wong et al., "Suppressive effects of methoxyflavonoids isolated from *Kaempferia parviflora* on inducible nitric oxide synthase (iNOS) expression in RAW 264.7 cells," Journal of Ethnopharmacology (2011), vol. 136, No. 3, pp. 488-495.

Shimada et al., "Kaempferia parviflora no Yakurigakuteki Kenkyu (2)—Metabolic Syndrome ni Taisuru Yobo Koka Oyobi Kassei Seibun no Tansaku-," Abstracts of the 128th Annual Meeting of Pharmaceutical Society of Japan, Mar. 5, 2008, p. 76.

Shimada et al., "*Kaempferia parviflora* no Yakurigakuteki Kenkyu (3)—Sakusan Ethyl Kakubun no Taishasei Shikkan ni Taisuru Yobo Koka-," Journal of Traditional Medicines (Aug. 7, 2009), vol. 26, Special Extra Issue, p. 92.

Shimada et al., "Preventive effect of *Kaempferia parviflora* ethyl acetate extract and its major components polymethoxyflavanoid on metabolic diseases," Fitoterapia (2011), vol. 82, pp. 1272-1278.

Sutthanut et al., "Simultaneous identification and quantitation of 11 flavonoid constituents in *Kaempferia parviflora* by gas chromatography," Journal of Chromatography A (2007), vol. 1143, pp. 227-233.

Washino et al., "Kuro Ukon no Metabolic Shokogun ni Taisuru Rinsho Koka," Abstracts of the 129th Annual Meeting of Pharmaceutical Society of Japan 2, Mar. 5, 2009, p. 164.

Yamaguchi et al., "Biological Characterization of Black Turmeric (*Kaempferia parviflora*) Using an in vitro Assay Panel," Japan Heath and Nutrition Food Association (2009), vol. 12, No. 2, pp. 29-35, with English abstract.

Extended European Search Report issued May 21, 2015, in European Patent Application No. 12861987.1.

Tewtrakul et al., "Anti-inflammatory effects of compounds from *Kaempferia parviflora* and *Boesenbergia pandurata*," Food Chemistry (2009), vol. 115, pp. 534-538.

Tewtrakul et al., "Effects of compounds from *Kaempferia parviflora* on nitric oxide, prostaglandin $E_2$ and tumor necrosis factor-alpha productions in RAW264.7 macrophage cells," Journal of Ethnopharmacology (2008), vol. 120, pp. 81-84.

Wongsrikaew et al., "Antiproliferative Activity and Polymethoxyflavone Composition Analysis of *Kaempferia parviflora* Extracts," J. Korean Soc. Appl. Biol. Chem. (2012), vol. 55, pp. 813-817.

Yenjai et al., "Bioactive flavonoids from *Kaempferia parviflora*," Fitoterapia (2004), vol. 75, pp. 89-92.

English translation of Abstracts of 128th Annual Meeting of Pharmaceutical Society of Japan, Mar. 5, 2008 p. 76.

English translation of Abstracts of 129th Annual Meeting of Pharmaceutical Society of Japan 2, Mar. 5, 2009 (Mar. 5, 2009), p. 164.

English translation of Journal of traditional medicines, Aug. 7, 2009, vol. 26, special extra issue, p. 92.

Machine English translation of JP 2003-192588 A (Jul. 9, 2003).
Machine English translation of JP 2004-083417 A (Mar. 18, 2014).
Machine English translation of JP 2005-206546 A (Aug. 4, 2005).
Machine English translation of JP 2009-051790 A (Mar. 12, 2009).
Machine English translation of JP 2009-067731 A (Apr. 2, 2009).
Machine English translation of JP 2010-209051 A (Sep. 24, 2010).
Machine English translation of JP 3010210 B (Dec. 10, 1999).

* cited by examiner

SIRTUIN ACTIVATOR

TECHNICAL FIELD

The present invention relates to a sirtuin activator comprising an active component composed of black ginger or a black ginger extract. Additionally, the present invention relates to a sirtuin activator that exhibits a stronger activity than resveratrol, specifically, to a sirtuin activator comprising an active component composed of a polyalkoxyflavonoid compound represented by general formula (I).

BACKGROUND ART

Sirtuin is a collective name for a group of $NAD^+$ dependant deacetylase, which is distributed in a wide range from bacteria to eukaryote, and various sirtuins have been identified including 5 types in yeast, such as Sir2, and 7 types in human (SIRT1 to SIRT7). Sirtuins in the cells are found in cytoplasm, mitochondria, etc., and they play an important part in the living body.

Sir2 was first found as a longevity gene of yeast, and it was subsequently proven to regulate aging/lifespan in the nematode and the fruitfly. There is a report that Sir2 provides a life lengthening effect through DNA repair and recombination by preventing acetylation of histone, which has a gene-protection effect (Non-Patent Document 1). The human SIRT1, which exhibits high homology with the yeast Sir2, is known to deacetylate lysine 382 of the p53 protein, associated with aging, to thereby regulate p53 and secure an anti-aging effect (Non-Patent Document 2). It is thus expected that an activation of SIRT1 would rejuvenate cells and prevent their aging, in other words, lengthen their lifespan.

Further, it is known that the waning of the oxidative phosphorylation reaction of mitochondria and the decrease in the amount and functionality of mitochondria, caused by obesity and aging, induce metabolic syndrome and diabetes. It is expected that when deacetylation of PGC-1α is accelerated through the activation of SIRT1, PGC-1α, as a transcription cofactor, would enhance the protein expression of GLUT4 and mitochondria, provide an anti-aging effect, and thus, improve metabolic syndrome and diabetes (Non-Patent Document 3).

SIRT1 activates endothelial NO synthase (eNOS) and induces endothelium dependent vasodilation, and in an experiment in which SIRT1 was overexpressed, the age-dependent left ventricle dysfunction was regulated; hence, an activated SIRT1 is expected to prevent aging of the cardiovascular systems and aging-related diseases. Additionally, SIRT1 regulates synthesis of gelatinase MMP-9 via NK-κB. Considering that MMP-9 decomposes collagen and induces inflammation, it can be determined that an activated SIRT1 would provide an anti-aging effect and an anti-inflammatory effect of the skin (Non-Patent Document 4).

While calorie regulation and a balanced diet constitute factors for activating a sirtuin gene, plant components and synthetic agonists that activate sirtuin are also seen with expectation. It has recently been reported that a polyphenol compound "resveratrol" contained in wines, etc., is effective in activating sirtuin (Non-Patent Document 5), and the effects of intaking a resveratrol-containing supplement, such as the regulation of aging, prevention of metabolic syndrome, or improvement of diabetes, are receiving attention. However, natural resveratrol that can be used in food is limited to certain resources, such as grape skin and grape leaf, and the content is extremely low, so a natural sirtuin-activating substance of a low price that is easier to obtain than resveratrol is awaited, and a stronger sirtuin activating substance is desired (Non-Patent Document 6).

*Kaempferia parviflora* is a plant in the genus *Kaempferia* of the plant family Zingiberaceae, which is also known as black ginger, Thai ginseng, or Kra chai dahm. Black ginger is cultivated widely in Thai, its country of origin, and it has been taken commonly from old, to be used in enhancing nutrition, enhancing (sexual) energy, reducing blood glucose level, recovering physical strength, and improving the circulatory system or the digestive system. Other effects of black ginger including anti-inflammatory effect (Non-Patent Document 7), effect of improving sensitivity to cold (Patent Document 1), cAMP-phosphodiesterase activation effect (Patent Document 2), antiallergic effect (Non-Patent Document 8) are reported by recent researches. However, there is no report to date of black ginger having an effect of activating sirtuin genes.

Further, flavonoid is a type of polyphenol, and it is a collective name of a series of plant pigments that exists widely in plants, such as vegetables and fruits, and that has a basic backbone of $C_6$—$C_3$—$C_6$. Flavonoid has been considered an unnecessary component until recently, but an advance in the research of the biological regulation function of food unfolded various physiological functions of flavonoid and made flavonoid one of the most popular food components.

Of the flavonoid compounds, those having many hydroxyl groups, namely, butein (3,4,2',4'-tetrahydroxychalcone), isoliquiritigenin (4,2',4'-trihydroxychalcone), fisetin (3,7,3',4'-tetrahydroxyflavone), quercetin (3,5,7,3',4'-pentahydroxyflavone), were reported as having a sirtuin activation activity, but their activity was weaker than resveratrol (Non-Patent Document 4).

Polyalkoxyflavonoid is a group of compounds that are flavonoids substituted with an alkoxy group at one or more of position 3, position 5, position 6, position 7, position 8, position 2', position 3' and position 4', and a polyalkoxyflavonoid substituted by a plurality of alkoxy groups (particularly, methoxy group) is reported (Non-Patent Documents 9 and 10). Polyalkoxyflavonoid is reported to have an antioxidant effect, anti-inflammation effect, androgen receptor binding inhibition effect (Patent Document 3), matrix metalloproteinase generation inhibition effect (Patent Document 4), UV ray inducing prostaglandin E2 generation regulation effect (Patent Document 5), vascularization regulation effect (Patent Document 6), etc. However, no report has yet been provided concerning sirtuin activation activity of polyalkoxyflavonoid.

CITATION LIST

Patent Documents

Patent Document 1: Japanese unexamined patent publication No. 2009-67731
Patent Document 2: Japanese unexamined patent publication No. 2009-51790
Patent Document 3: Japanese unexamined patent publication No. 2005-206546
Patent Document 4: Japanese patent No. 3010210
Patent Document 5: Japanese unexamined patent publication No. 2003-192588
Patent Document 6: Japanese unexamined patent publication No. 2004-83417

Non-Patent Documents

Non-Patent Document 1: The silencing protein SIR2 and its homologs are NAD-dependent protein deacetylase. Proc. Natl. Acad. Sci. USA., 97: 5807-5811, 2000.

Non-Patent Document 2: Human SIR2 deacetylates p53 and antagonizes PML/p53-induced cellular senescence. EMBO J., 21: 2383-2396, 2002.

Non-Patent Document 3: Adiponectin and AdipoR1 regulate PGC-1 and mitochondria by $Ca^{2+}$ and AMPK/SIRT1. Nature, 464: 1313-1319, 2010.

Non-Patent Document 4: Aging and disease: connections to sirtuins. Aging cell, 9: 285-290, 2010.

Non-Patent Document 5: Small molecule activators of sirtuins extend *Saccharomyces cerevisiae* lifespan. Nature, 425: 191-196, 2003.

Non-Patent Document 6: Trans-resveratrol concentrations in berry skins and wines from grapes grown in Japan. Am. J. Enol. Vitic., 47(1): 93-99, 1996.

Non-Patent Document 7: Suppressive effects of methoxyflavonoids isolated from *Kaempferia parviflora* on inducible nitric oxide synthase (iNOS) expression in RAW 274.7 cells. Journal of Ethnopharmacology, 136(3): 488-495, 2011.

Non-Patent Document 8: Assessment of Physiological Activity of black ginger (*Kaempferia parviflora*) by In vitro Assay, Japan Health and Nutrition Food Association, 12(2): 29-35, 2009.

Non-Patent Document 9: Preventive effect of *Kaempferia parviflora* ethyl acetate extract and its major components polymethoxy flavonoid on metabolic diseases. Fitoterapia, 82: 1271-1278, 2011.

Non-Patent Document 10: Simultaneous identification and quantitation of 11 flavonoid constituents in *Kaempferia parviflora* by gas chromatography. Journal of Chromatography A, 1143: 227-233, 2007.

SUMMARY OF INVENTION

Technical Problem

The present invention is directed to providing a sirtuin activator.

Solution to Problem

As a result of conducting intensive studies to solve the above problem and achieve the object of the present invention, the present inventors found that black ginger or a black ginger extract has a sirtuin activation effect and constitutes a sirtuin activator, and thus, the present invention was completed. Further, the present inventors conducted an intensive search for various compounds and natural substances, and found that the polyalkoxyflavonoid compound has a sirtuin activation activity which is 10 folds the strength of the publicly known resveratrol or higher; thus, the invention was completed.

Sirtuin activators of (1) to (12) below are provided according to an aspect of the present invention.

(1) A sirtuin activator comprising an active component composed of black ginger or a black ginger extract.

(2) The sirtuin activator according to (1) above, wherein black ginger is a plant having a nomenclature of *Kaempferia parviflora*.

(3) The sirtuin activator according to either (1) or (2) above comprising an active component composed of an extract from black ginger obtained by a solvent.

(4) The sirtuin activator according to (3) above, wherein the solvent is selected from water, methanol, ethanol, propanol, isopropanol, butanol, isobutanol, ethyl acetate, or a combination thereof.

(5) The sirtuin activator according to (4) above, wherein the solvent is ethanol.

(6) The sirtuin activator according to (5) above, wherein ethanol is a water-containing ethanol having an ethanol content of 30% to 95% (v/v).

(7) The sirtuin activator according to either (1) or (2) above comprising an active component composed of an extract from black ginger obtained by a water-containing hydrophilic solvent.

(8) The sirtuin activator according to (7) above, wherein the water-containing hydrophilic solvent is ethanol.

(9) The sirtuin activator according to (8) above, wherein ethanol is a water-containing ethanol having an ethanol content of 30% to 95% (v/v).

(10) The sirtuin activator according to (1) above, wherein black ginger is a plant having a nomenclature of *Kaempferia parviflora*, which is native to Southeast Asia including Thai or Laos, or is cultivated in Okinawa.

(11) The sirtuin activator according to (1), (2) or (10) above, wherein a black ginger extract is an extract from black ginger obtained by a water-containing hydrophilic solvent.

(12) The sirtuin activator according to (11) above, wherein the water-containing hydrophilic solvent is a water-containing ethanol having an ethanol content of 30% to 95% (v/v).

A preventative agent of (13) below is provided according to a different aspect of the present invention.

(13) A metabolic syndrome preventative agent comprising the sirtuin activator according to any one of (1) to (12) above.

An insulin resistance improving agent of (14) below is provided according to another different aspect of the present invention.

(14) An insulin resistance improving agent comprising the sirtuin activator according to any one of (1) to (12) above.

An anti-aging agent of (15) below is provided according to another different aspect of the present invention.

(15) An anti-aging agent comprising the sirtuin activator according to any one of (1) to (12) above.

A life-lengthening agent of (16) below is provided according to another different aspect of the present invention.

(16) The life-lengthening agent comprising the sirtuin activator according to any one of (1) to (12) above.

A food and drink, cosmetics, or pharmaceutical composition of (17) below is provided according to another different aspect of the present invention.

(17) A food and drink, cosmetics, or pharmaceutical composition comprising a sirtuin activator according to any one of (1) to (12) above.

A use of (18) to (22) below is provided according to another different aspect of the present invention.

(18) A use of black ginger or a black ginger extract in the production of a sirtuin activator.

(19) A use of black ginger or a black ginger extract in the production of a metabolic syndrome preventative agent.

(20) A use of black ginger or a black ginger extract in the production of an insulin resistance improving agent.

(21) A use of black ginger or a black ginger extract in the production of an anti-aging agent.

(22) A use of black ginger or a black ginger extract in the production of a life-lengthening agent.

The methods of (23) to (27) below are provided according to another different aspect of the present invention.

(23) A method for activating sirtuin by administering black ginger or a black ginger extract to the subject.

(24) A method for preventing metabolic syndrome by administering black ginger or a black ginger extract to the subject.

(25) A method for improving insulin resistance by administering black ginger or a black ginger extract to the subject.

(26) A method for preventing aging by administering black ginger or a black ginger extract to the subject.

(27) A method for lengthening aging by administering black ginger or a black ginger extract to the subject.

A sirtuin activator of (28) to (30) below is provided according to another different aspect of the present invention.

(28) A sirtuin activator comprising an active component composed of a polyalkoxyflavonoid compound represented by general formula (I):

[Formula 1]

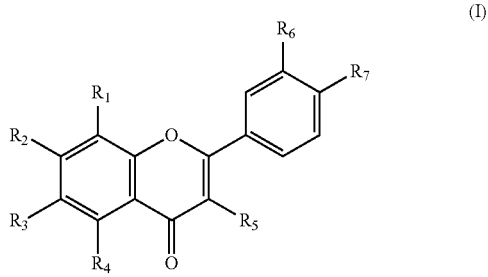

wherein, $R_1$ to $R_7$ are each independently a hydrogen atom, a hydroxyl group, or a C1 to C6 lower alkoxy group.

(29) The sirtuin activator according to (28) above, wherein the polyalkoxyflavonoid compound is a polymethoxyflavonoid compound represented by general formula (II):

[Formula 2]

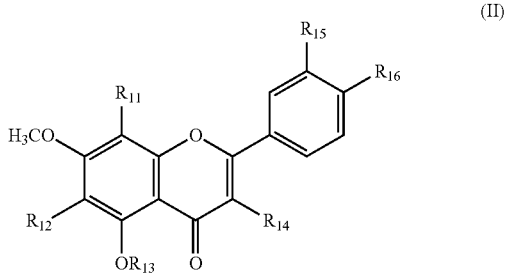

wherein $R_{11}$, $R_{12}$, $R_{14}$, $R_{15}$ and $R_{16}$ are each independently a hydrogen atom, a hydroxyl group, or methoxy, and $R_{13}$ is a hydrogen atom or a methyl group.

(30) The sirtuin activator according to (28) or (29) above, wherein the compound of general formula (I) or (II) is selected from a group consisting of apigenin-5,7,4'-trimethylether, quercetin-3,5,7,3',4'-pentamethylether, chrysin dimethylether, 3,5,7,4'-tetramethoxyflavone, and 3,5,7-trimethoxyflavone.

A preventative agent, an anti-aging agent, an anti-inflammatory agent according to (31) below is provided according to another different aspect of the present invention.

(31) A metabolic syndrome preventative agent, an anti-aging agent, a cancer preventative agent, a cardiovascular disease preventative agent, or an anti-inflammatory agent comprising a sirtuin activator according to any one of (28) to (30) above.

An insulin resistance improving agent according to (32) below is provided according to another different aspect of the present invention.

(32) An insulin resistance improving agent comprising the sirtuin activator according to any one of (28) to (30) above.

A life-lengthening agent according to (33) below is provided according to another different aspect of the present invention.

(33) A life-lengthening agent comprising a sirtuin activator according to any one of (28) to (30) above.

A food and drink, a health food, cosmetics, or a pharmaceutical composition according to (34) below is provided according to another aspect of the present invention.

(34) A food and drink, a health food, cosmetics, or a pharmaceutical composition comprising a sirtuin activator according to any one of (28) to (30) above.

A use according to (35) to (46) below is provided according to another aspect of the present invention.

(35) A use of a polyalkoxyflavonoid compound represented by general formula (I) in the production of a sirtuin activator:

[Formula 3]

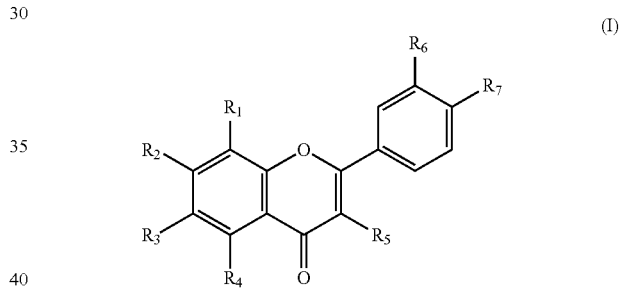

wherein, $R_1$ to $R_7$ are each independently a hydrogen atom, a hydroxyl group, or a C1 to C6 lower alkoxy group.

(36) The use according to (35) above, wherein the polyalkoxyflavonoid compound is a polymethoxyflavonoid compound represented by general formula (II):

[Formula 4]

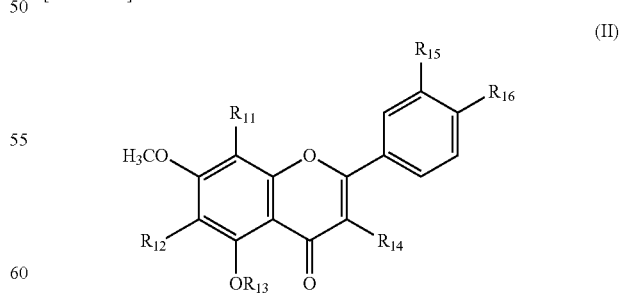

wherein $R_{11}$, $R_{12}$, $R_{14}$, $R_{15}$ and $R_{16}$ are each independently a hydrogen atom, a hydroxyl group, or methoxy, and $R_{13}$ is a hydrogen atom or a methyl group.

(37) The use according to (35) or (36) above, wherein the compound of general formula (I) or (II) is selected from a group consisting of apigenin-5,7,4'-trimethylether, quercetin-3,5,7,3',4'-pentamethylether, chrysin dimethylether, 3,5,7,4'-tetramethoxyflavone, and 3,5,7-trimethoxyflavone.

(38) A use of a polyalkoxyflavonoid compound represented by general formula (I) in the production of a metabolic syndrome preventative agent, an anti-aging agent, a cancer preventative agent, a cardiovascular disease preventative agent, or an anti-inflammatory agent:

[Formula 5]

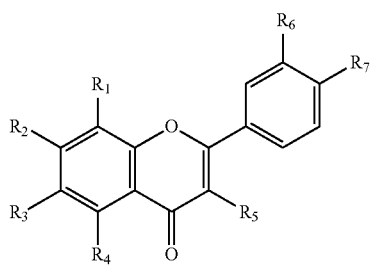

(I)

wherein, $R_1$ to $R_7$ are each independently a hydrogen atom, a hydroxyl group, or a C1 to C6 lower alkoxy group.

(39) The use according to (38) above, wherein the polyalkoxyflavonoid compound is a polymethoxyflavonoid compound represented by general formula (II):

[Formula 6]

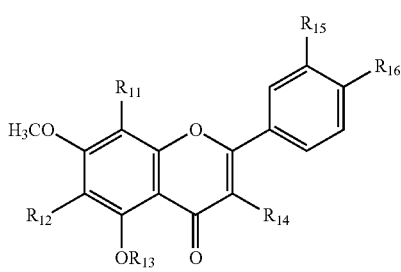

(II)

wherein $R_{11}$, $R_{12}$, $R_{14}$, $R_{15}$ and $R_{16}$ are each independently a hydrogen atom, a hydroxyl group, or methoxy, and $R_{13}$ is a hydrogen atom or a methyl group.

(40) The use according to (38) or (39) above, wherein the compound of general formula (I) or (II) is selected from a group consisting of apigenin-5,7,4'-trimethylether, quercetin-3,5,7,3',4'-pentamethylether, chrysin dimethylether, 3,5,7,4'-tetramethoxyflavone, and 3,5,7-trimethoxyflavone.

(41) A use of a polyalkoxyflavonoid compound represented by general formula (I) in the production of an insulin resistance improving agent:

[Formula 7]

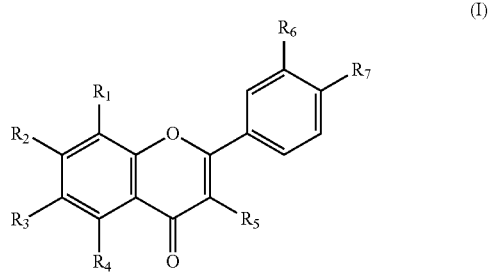

(I)

wherein, $R_1$ to $R_7$ are each independently a hydrogen atom, a hydroxyl group, or a C1 to C6 lower alkoxy group.

(42) The use according to (41) above, wherein the polyalkoxyflavonoid compound is a polymethoxyflavonoid compound represented by general formula (II):

[Formula 8]

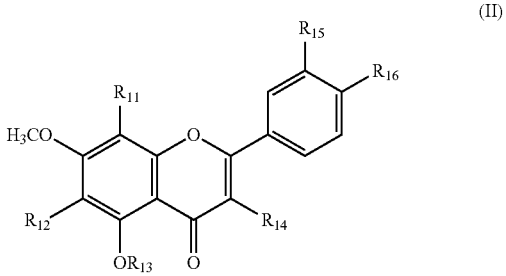

(II)

wherein $R_{11}$, $R_{12}$, $R_{14}$, $R_{15}$ and $R_{16}$ are each independently a hydrogen atom, a hydroxyl group, or methoxy, and $R_{13}$ is a hydrogen atom or a methyl group.

(43) The use according to (41) or (42) above, wherein the compound of general formula (I) or (II) is selected from a group consisting of apigenin-5,7,4'-trimethylether, quercetin-3,5,7,3',4'-pentamethylether, chrysin dimethylether, 3,5,7,4'-tetramethoxyflavone, and 3,5,7-trimethoxyflavone.

(44) A use of a polyalkoxyflavonoid compound represented by general formula (I) as an active component in the production of a life-lengthening agent:

[Formula 9]

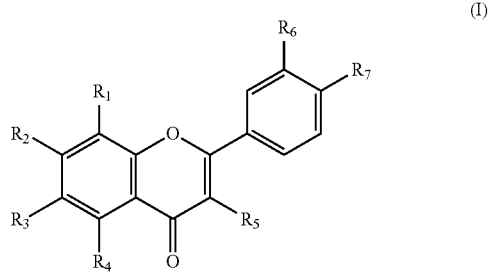

(I)

wherein, $R_1$ to $R_7$ are each independently a hydrogen atom, a hydroxyl group, or a C1 to C6 lower alkoxy group.

(45) The use according to (44) above, wherein the polyalkoxyflavonoid compound is a polymethoxyflavonoid compound represented by general formula (II):

[Formula 10]

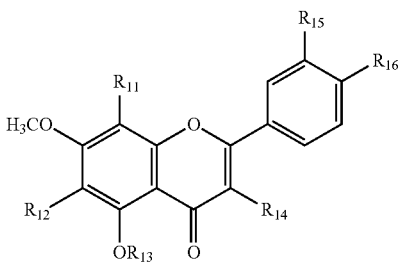

(II)

wherein $R_{11}$, $R_{12}$, $R_{14}$, $R_{15}$ and $R_{16}$ are each independently a hydrogen atom, a hydroxyl group, or methoxy, and $R_{13}$ is a hydrogen atom or a methyl group.

(46) The use according to (44) or (45) above, wherein the compound of general formula (I) or (II) is selected from a group consisting of apigenin-5,7,4'-trimethylether, quercetin-3,5,7,3',4'-pentamethylether, chrysin dimethylether, 3,5,7,4'-tetramethoxyflavone, and 3,5,7-trimethoxyflavone.

The methods according to (47) to (58) below according to another different aspect of the present invention.

(47) A method of activating sirtuin by administering a polyalkoxyflavonoid compound represented by general formula (I) to the subject:

[Formula 11]

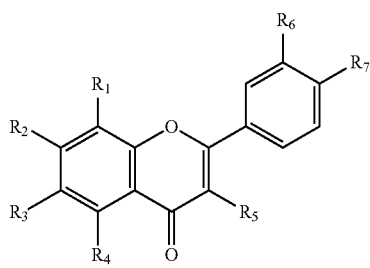

(I)

wherein, $R_1$ to $R_7$ are each independently a hydrogen atom, a hydroxyl group, or a C1 to C6 lower alkoxy group.

(48) The method according to (47) above, wherein the polyalkoxyflavonoid compound is a polymethoxyflavonoid compound represented by general formula (II):

[Formula 12]

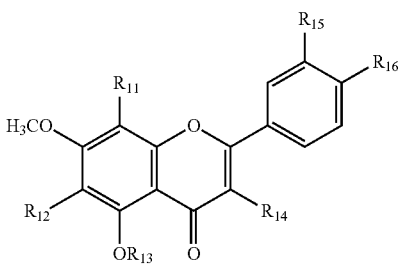

(II)

wherein $R_{11}$, $R_{12}$, $R_{14}$, $R_{15}$ and $R_{16}$ are each independently a hydrogen atom, a hydroxyl group, or methoxy, and $R_{13}$ is a hydrogen atom or a methyl group.

(49) The method according to (47) or (48) above, wherein the compound of general formula (I) or (II) is selected from a group consisting of apigenin-5,7,4'-trimethylether, quercetin-3,5,7,3',4'-pentamethylether, chrysin dimethylether, 3,5,7,4'-tetramethoxyflavone, and 3,5,7-trimethoxyflavone.

(50) A method of preventing a metabolic syndrome, preventing aging, preventing cancer, preventing a cardiovascular disease, or preventing inflammation by administering a polyalkoxyflavonoid compound represented by general formula (I) to the subject:

[Formula 13]

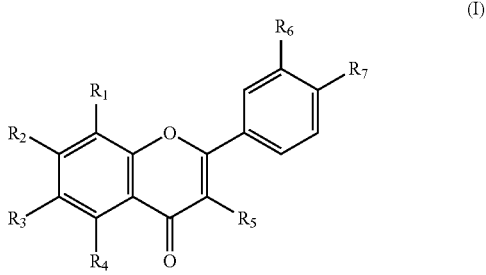

(I)

wherein, $R_1$ to $R_7$ are each independently a hydrogen atom, a hydroxyl group, or a C1 to C6 lower alkoxy group.

(51) The method according to (50) above, wherein the polyalkoxyflavonoid compound is a polymethoxyflavonoid compound represented by general formula (II):

[Formula 14]

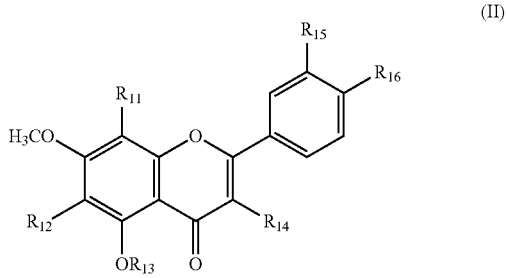

(II)

wherein $R_{11}$, $R_{12}$, $R_{14}$, $R_{15}$ and $R_{16}$ are each independently a hydrogen atom, a hydroxyl group, or methoxy, and $R_{13}$ is a hydrogen atom or a methyl group.

(52) The method according to (50) or (51) above, wherein the compound of general formula (I) or (II) is selected from a group consisting of apigenin-5,7,4'-trimethylether, quercetin-3,5,7,3',4'-pentamethylether, chrysin dimethylether, 3,5,7,4'-tetramethoxyflavone, and 3,5,7-trimethoxyflavone.

(53) A method of improving insulin resistance by administering a polyalkoxyflavonoid compound represented by general formula (I) to the subject:

[Formula 15]

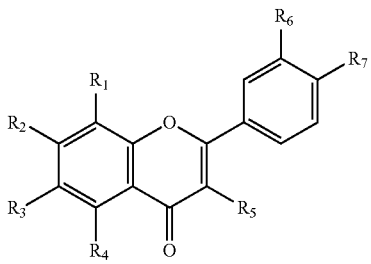

(I)

wherein, $R_1$ to $R_7$ are each independently a hydrogen atom, a hydroxyl group, or a C1 to C6 lower alkoxy group.

(54) The method according to (53) above, wherein the polyalkoxyflavonoid compound is a polymethoxyflavonoid compound represented by general formula (II):

[Formula 16]

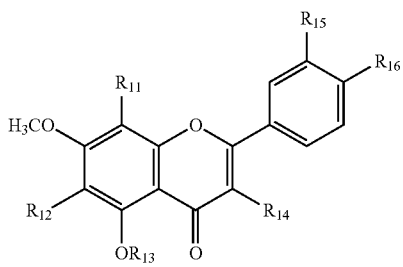

(II)

wherein $R_{11}$, $R_{12}$, $R_{14}$, $R_{15}$ and $R_{16}$ are each independently a hydrogen atom, a hydroxyl group, or methoxy, and $R_{13}$ is a hydrogen atom or a methyl group.

(55) The method according to (53) or (54) above, wherein the compound of general formula (I) or (II) is selected from a group consisting of apigenin-5,7,4'-trimethylether, quercetin-3,5,7,3',4'-pentamethylether, chrysin dimethylether, 3,5,7,4'-tetramethoxyflavone, and 3,5,7-trimethoxyflavone.

(56) A method of lengthening life by administering a polyalkoxyflavonoid compound represented by general formula (I) to the subject:

[Formula 17]

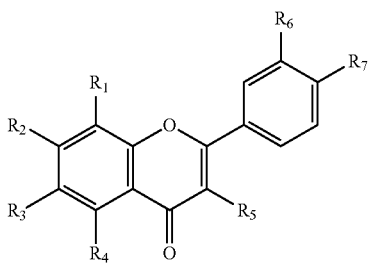

(I)

wherein, $R_1$ to $R_7$ are each independently a hydrogen atom, a hydroxyl group, or a C1 to C6 lower alkoxy group.

(57) The method according to (56) above, wherein the polyalkoxyflavonoid compound is a polymethoxyflavonoid compound represented by general formula (II):

[Formula 18]

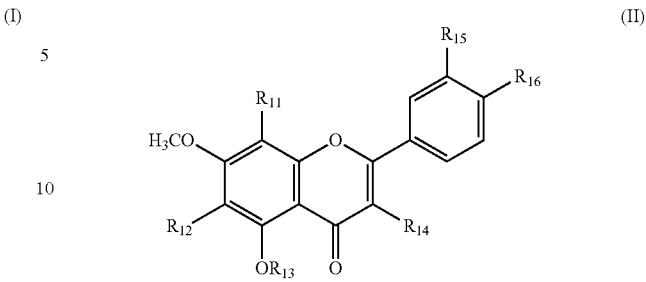

(II)

wherein $R_{11}$, $R_{12}$, $R_{14}$, $R_{15}$ and $R_{16}$ are each independently a hydrogen atom, a hydroxyl group, or methoxy, and $R_{13}$ is a hydrogen atom or a methyl group.

(58) The method according to (56) or (57) above, wherein the compound of general formula (I) or (II) is selected from a group consisting of apigenin-5,7,4'-trimethylether, quercetin-3,5,7,3',4'-pentamethylether, chrysin dimethylether, 3,5,7,4'-tetramethoxyflavone, and 3,5,7-trimethoxyflavone.

DESCRIPTION OF EMBODIMENTS

Figure 1:
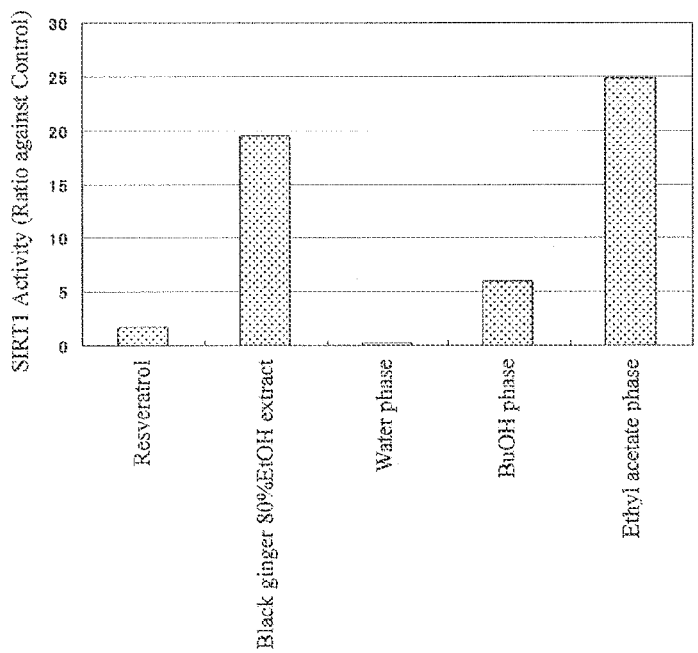
FIG. 1 is a diagram showing a result of studying the sirtuin activity acceleration effect using SIRT1 for each added subject sample in Example 3.

It is possible to use a rhizome of *Kaempferia parviflora*, which is native to Southeast Asia including Thai or Laos, or is cultivated in Okinawa, as the black ginger of the present invention. Further, a black ginger that is raw, dried or processed from rhizome can be used, and the underground part of black ginger including the rhizome can be used as-is.

The method for extracting a black ginger extract is not particularly limited, and extraction can be performed by a method well known to a person skilled in the art. Water or warm water, alcoholic solvents, and acetone or other organic solvents can be used as the extracting solvent. Examples of alcoholic solvents include methanol, ethanol, propanol, isopropanol, butanol, and isobutanol. Examples other than acetone of other organic solvents include esters, such as ethyl acetate; polyols, such as ethylene glycol, propylene glycol, 1,3-butylene glycol; ethers, such as diethyl ether.

These solvents can be used alone or in combination. The extracting solvent can be used in the form of a water-containing hydrophilic solvent that combines water and a hydrophilic organic solvent. When using solvents in combination, the mix ratio of the solvents can be set arbitrarily. The solvent that is preferable for use, among those given, is ethanol, and that which is more preferable is a water-containing ethanol having an ethanol content of 30% to 95% (v/v).

The amount of extracting solvent should preferably be 2 to 100 weight parts against the dry weight of black ginger rhizome. The extraction temperature should preferably be 4 to 90° C. The extraction time should preferably be 30 minutes to 1 week. Extraction can be performed by any extraction method including agitation extraction, immersion extraction, counterflow extraction, ultrasound extraction, and supercritical extraction.

The black ginger extract includes a filtrate obtained by filtering the obtained liquid extract, or a liquid concentrate obtained by concentrating the filtrate, a dried matter obtained by drying the liquid concentrate, or a partially-refined product or a refined product thereof. Concentration can be performed by any concentration method including evaporation concentration, or membrane concentration. Drying can be performed by any drying method including decompression drying, freeze drying, spray drying. Excipients, such as dextrin, can be added as necessary. Refining can be performed by a means known to a person skilled in the art. Exemplary matters that can be used therein include synthetic-adsorption resin, activated carbon, ion-exchange resin, gel filtration agents, such as sephadex, biogel, column chromatography, recrystallization, used alone or in combination.

Further, the black ginger extract of the present invention can be obtained by performing extraction, two or more times, using different solvents. The extracting solvent, the amount of the extracting solvent, the concentration method, the drying method, and the refining method for such extraction, performed two or more times, are exactly as previously described in the present specification. For example, in an extraction performed twice, an extract is obtained by extraction from black ginger using an extracting solvent, then, the extract is subjected to further extraction using a different extracting solvent to obtain the targeted black ginger extract. In the method of obtaining the targeted black ginger extract by performing extraction twice, the extracting solvent in the first extraction step is preferably a water-containing alcohol, more preferably a water-containing ethanol. The water-containing ethanol is preferably a water-containing ethanol having an ethanol content of 30% to 95% (v/v), more preferably a water-containing ethanol having an ethanol content of 30% to 85% (v/v), and most preferably a water-containing ethanol of 80% (v/v). Meanwhile, the extracting solvent in the second extraction step in the method of obtaining the targeted black ginger extract by performing extraction twice can be selected from water, methanol, propanol, isopropanol, butanol, isobutanol, ethyl acetate, or a combination thereof, of which water, butanol, or ethyl acetate is preferable, and the second extraction step can be performed, for example, using ethyl acetate as the extracting solvent. The extraction temperature and the extraction time in the method of obtaining the targeted black ginger extract by performing extraction twice are not particularly limited, and the first extraction step can be performed under heated reflux, while the second extraction step is performed without heated reflux. The extraction of two or more times using different solvents as explained above enables a more efficient production of an active component that exhibits sirtuin activity.

The black ginger extract of the present invention can also be obtained in an aspect of the present invention through a first step of obtaining an extract by extraction from black ginger using an extracting solvent, and a second step of partitioning the extract using water and an organic solvent. The extracting solvent, the amount of the extracting solvent, the concentration method, the drying method, and the refining method in the first step are exactly as already described in the present specification. The extraction temperature and the extraction time in the first step are not particularly limited, and the extraction can be performed under heated reflux. The organic solvent that can be used in the partitioning of the second step can be selected from propanol, isopropanol, butanol, isobutanol, ethyl acetate or a combination thereof, preferably from butanol or ethyl acetate, and the partitioning in the second step can be performed, for example, by using ethyl acetate as an organic solvent. The amount of water and organic solvent, the partitioning temperature, and the partitioning time are not particularly limited as long as the desired black ginger extract can be partitioned.

The present invention further provides a metabolic syndrome preventative agent, an insulin resistance improving agent, an anti-aging agent, and a life-lengthening agent containing a sirtuin activator that comprises an active component composed of black ginger, or a black ginger extract.

The present invention further provides a sirtuin activator produced by extraction from black ginger, and a metabolic syndrome preventative agent, an insulin resistance improving agent, an anti-aging agent, and a life-lengthening agent containing such sirtuin activator. The method for extraction from black ginger in the production of the sirtuin activator is exactly as already described in the present specification, and the extraction can be performed twice using different solvents to produce the sirtuin activator.

The administration method of the metabolic syndrome preventative agent, the insulin resistance improving agent, the anti-aging agent, and the life-lengthening agent of the present invention is not particularly limited, but a dosage form that enables oral administration is preferable. The form of the metabolic syndrome preventative agent, the insulin resistance improving agent, the anti-aging agent, and the life-lengthening agent of the present invention is not particularly limited, but to allow oral administration, it can take the form of tablet, capsule, powder, granule, pill, liquid formulation, emulsion, suspension, solution agent, spirit, syrup, extract, elixir, for example. Further, a pharmaceutical formulation can have various pharmaceutically acceptable carriers added thereto, which may include an excipient, a binder, a disintegrator, a lubricant, a flavoring agent, a coloring agent, a sweetener, a corrective, a solubilizer, a suspending agent, an emulsifying agent, a coating agent, and an antioxidant, without being limited thereby.

The present invention further provides a composition having a sirtuin activating effect including black ginger or a black ginger extract, and the composition may be provided as a food and drink, health foods, cosmetics or medicines.

The form of the composition of the present invention when it is food and drink or health food is not particularly limited, and the present invention can be formed as noodles, bread, candy, jelly, cookie, soup or health drinks by adding black ginger or a black ginger extract to the raw material. Note that such food and drink may incorporate inorganic materials, such as iron, calcium, various vitamins, oligosaccharides, dietary fiber such as chitosan, protein such as soy bean extract, fat such as lecithin, sugars such as sucrose, or milk sugar, in addition to black ginger or a black ginger extract, in a range that achieves the object of the present invention, as necessary.

The form of the composition of the present invention as cosmetics is not particularly limited, and possible exemplary forms of use include lotion, latex, cream, poultice, pack, soap. Note that such cosmetics can appropriately incorporate components that are used commonly in cosmetics, other than black ginger or a black ginger extract, in a range that achieves the object of the present invention. Examples of such components include oil, wetting agent, UV absorber, oxidation preventative agent, surfactant, antiseptic, humectants, plant extract, fragrance, water, alcohol, thickener, etc.

The administration method of the composition of the present invention as a medicine is not particularly limited, but an orally administrable dosage form is preferable. The form of the composition of the present invention as a medicine is not particularly limited, but to allow oral administration, it can take the form of tablet, capsule, powder, granule, pill, liquid formulation, emulsion, suspension, solution agent, spirit, syrup, extract, elixir, for example. Further, a pharmaceutical formulation can have various pharmaceutically acceptable carriers added thereto, which may include an excipient, a binder, a disintegrator, a lubricant, a flavoring agent, a coloring agent, a sweetener, a corrective, a solubilizer, a suspending agent, an emulsifying agent, a coating agent, and an antioxidant, without being limited thereby.

The amount of the pharmaceutical composition of the present invention to be administered to the subject is generally a daily dosage of 0.01 mg to 2000 mg, preferably 0.1 mg to 1000 mg, more preferably 1 mg to 500 mg, when converted to the amount of black ginger or a black ginger extract. The pharmaceutical composition of the present invention can be administered multiple times a day by dividing the daily dosage into portions. It can also be administered in combination with other agents and therapeutic methods.

The subject in the present invention is a mammal, such as human, cow, horse, cat, mouse, rat, etc., of which human is preferable.

The polyalkoxyflavonoid compound used in the present invention is a compound represented by the following general formula (I):

[Formula 19]

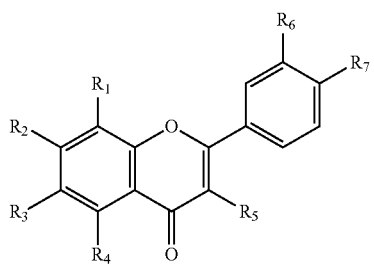

(I)

wherein, $R_1$ to $R_7$ is each independently a C1 to C6 lower alkoxy group, a hydrogen atom or a hydroxyl group.

A C1 to C6 lower alkoxy group in $R_1$ to $R_7$ of general formula (I) is a C1 to C6 alkyl group that binds to an oxygen atom by an ether linkage. The C1 to C6 lower alkoxy group is composed of a methoxy group, an ethoxy group, a propoxy group, a butoxy group, a pentoxy group, a hexoxy group, or a constitutional isomer thereof, and the methoxy group is preferable.

A preferable polyalkoxyflavonoid compound is a polymethoxyflavonoid compound, and a more preferable polymethoxyflavonoid compound is represented by the following general formula (II):

[Formula 20]

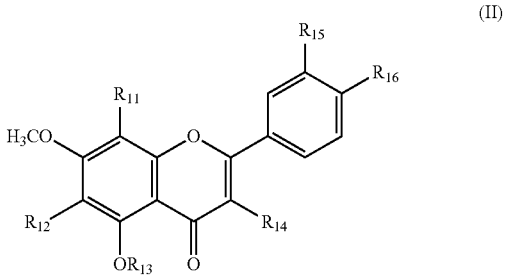

(II)

wherein $R_{11}$, $R_{12}$, $R_{14}$, $R_{15}$ and $R_{16}$ are each independently a hydrogen atom, a hydroxyl group or methoxy, and $R_{13}$ is a hydrogen atom or a methyl group.

Specific examples of a compound represented by the above general formula (II) are shown in Table 1 below.

TABLE 1

| Compound No | Compound Name | $R_{11}$ | $R_{12}$ | $R_{13}$ | $R_{14}$ | $R_{15}$ | $R_{16}$ |
|---|---|---|---|---|---|---|---|
| 1 | apigenin-5,7,4'-trimethylether | H | H | $CH_3$ | H | H | $OCH_3$ |
| 2 | quercetin-3,5,7,3',4'-pentamethylether | H | H | $CH_3$ | $OCH_3$ | $OCH_3$ | $OCH_3$ |
| 3 | chrysin dimethylether | H | H | $CH_3$ | H | H | H |
| 4 | 3,5,7,4'-tetramethoxyflavone | H | H | $CH_3$ | $OCH_3$ | H | $OCH_3$ |
| 5 | 3,5,7-trimethoxyflavone | H | H | $CH_3$ | $OCH_3$ | H | H |

The polyalkoxyflavonoid compound of the above general formula (I) or (II) can be obtained not only by chemical synthesis, but also by extraction/refining from *citrus* or *Kaempferia parviflora*, a plant in the genus *Kaempferia* of the family Zingiberaceae. Note that the synthetic method is not particularly limited, and a conventionally known method can be used.

Black ginger is a plant in the genus *Kaempferia* of the family Zingiberaceae, and its nomenclature is *Kaempferia parviflora*. *Kaempferia parviflora* is native to Southeast Asia including Thai or Laos, and it is known as black ginger, or Thai ginseng or Kra chai dahm. *Citrus* can be selected from a group consisting of *Citrus depressa, C. tachibana, C. leiocarpa, C. tardiva, C. succosa, C. suhuiensis, C. kinokuni, C. erythrosa, C. sunki, C. deliciosa, C. nobilis, C. retuculata, C. tangerina* belonging to the *citrus* division and *C. hanayu, C. nippokoreana* belonging to the yuzu division.

There is no particular limitation to which section of black ginger should be used, but it is especially preferable to use rhizome, since this section contains much active component. Black ginger can be used raw, dried or as a product processed from rhizome. Also, the underground part of black ginger including the rhizome can be used as-is. The sections to be used in a *citrus* include the fruit, the fruit skin, leaves, etc., and the fruit or the fruit skin is preferable for use as the subject to be extracted from. The fruit should preferably be used in its entirety including the fruit skin. The fruit or fruit skin to be used may be either an unripe fruit or its fruit skin or a ripe fruit or its fruit skin.

The extraction method is not particularly limited, and extraction can be performed by a method well known to a person skilled in the art. Water or warm water, alcoholic solvents, and acetone or other organic solvents can be used as the extracting solvent. Examples of alcoholic solvents include methanol, ethanol, propanol, isopropanol, butanol, and isobutanol. Examples other than acetone of other organic solvents include esters, such as ethyl acetate; polyols, such as ethylene glycol, propylene glycol, 1,3-butylene glycol; ethers, such as diethyl ether. These solvents can be used alone or in combination. The extracting solvent can be used in the form of a water-containing hydrophilic solvent that combines water and a hydrophilic organic solvent. When combining solvents for use, the mix ratio of the solvents can be set arbitrarily. The solvent that is preferable for use, among those given, is ethanol, and that which is more preferable is a water-containing ethanol having an ethanol content of 30% to 95% (v/v).

The amount of extracting solvent should preferably be 2 to 100 weight parts against the dry weight of black ginger rhizome. The extraction temperature should preferably be 4 to 90° C. The extraction time should preferably be 30 minutes to 1 week. Extraction can be performed by any extraction method including agitation extraction, immersion extraction, counterflow extraction, ultrasound extraction, and supercritical extraction.

Polyalkoxyflavonoid compounds can be refined by a means known to a person skilled in the art, using a liquid extract obtained through extraction by the above solvent, or a concentrated extract. Exemplary matters that can be used therein include synthetic-adsorption resin, activated carbon, ion-exchange resin, gel filtration agents, such as sephadex, biogel, column chromatography, recrystallization, used alone or in combination.

The structure of the polyalkoxyflavonoid compound obtained by refining can be identified using means known to a person skilled in the art. For example, the proton nuclear magnetic resonance spectroscopy ($^1$H-NMR), the carbon nuclear magnetic resonance spectroscopy ($^{13}$C-NMR), mass spectrometry (MS), elemental analysis, infrared spectroscopy (IR), ultraviolet spectroscopy (UV), melting point determination, can be used alone or in combination.

The present invention further provides a metabolic syndrome preventative agent, an anti-aging agent, cancer preventative agent, a cardiovascular disease preventative agent, or an anti-inflammatory agent, an insulin resistance improving agent, and a life-lengthening agent containing a sirtuin activator having the above polyalkoxyflavonoid compounds as the active component.

Since the polymethoxyflavonoid compounds of the present invention are also obtained by extraction/refining from black ginger, the above black ginger extract of the present invention can be used not only as a metabolic syndrome preventative agent, an insulin resistance improving agent, an anti-aging agent, and a life-lengthening agent, but also as a cancer preventative agent, a cardiovascular disease preventative agent, and an anti-inflammatory agent.

The administration method of the metabolic syndrome preventative agent, the anti-aging agent, the cancer preventative agent, the cardiovascular disease preventative agent, the anti-inflammatory agent, the insulin resistance improving agent, and the life-lengthening agent of the present invention is not particularly limited, but a dosage form that enables oral administration is preferable. The form of the metabolic syndrome preventative agent, the anti-aging agent, the cancer preventative agent, the cardiovascular disease preventative agent, the anti-inflammatory agent, the insulin resistance improving agent, and the life-lengthening agent of the present invention is not particularly limited, and the examples of forms for oral administration is as already mentioned in the present specification. Further, various pharmaceutically acceptable carriers can be added to pharmaceutical formulations, and examples of carriers are as already mentioned in the present specification.

The present invention further provides a composition having a sirtuin activating effect that includes the above polyalkoxyflavonoid compound, and the composition may be in the form of a food and drink, health food, cosmetics and medicines.

The form of a composition of the present invention as a food and drink or health food is not particularly limited, and exemplary forms of incorporating polyalkoxyflavonoid compounds to raw materials are as already mentioned in the present specification. Note that components other than the above polyalkoxyflavonoid compounds to be incorporated in the food and drink or health food are exactly as mentioned above in the present specification.

The form of a composition of the present invention as cosmetics is not particularly limited, and exemplary forms of cosmetics are as already mentioned in the present specification. Note that components other than polyalkoxyflavonoid compounds to be incorporated in the cosmetics are exactly as mentioned above in the present specification.

The method of administration of a composition of the present invention as a medicine is not particularly limited, but a dosage form that enables oral administration is preferable. The form of a composition of the present invention as a medicine is not particularly limited, and exemplary forms of medicines for oral administration are as mentioned in the present specification. Further, the pharmaceutical formulation can incorporate various pharmaceutically acceptable carriers, and exemplary carriers are as mentioned above in the present specification.

The amount of the pharmaceutical composition of the present invention to be administered to the subject is generally a daily dosage of 0.001 mg to 2000 mg, preferably 0.01 mg to 1000 mg, more preferably 0.1 mg to 500 mg, when converted to the amount of the above polyalkoxyflavonoid compounds. The pharmaceutical composition of the present invention can be administered multiple times a day by dividing the daily dosage into portions. It can also be administered in combination with other agents and therapeutic methods.

The subject in the present invention is exactly as already mentioned in the present specification.

EXAMPLES

The present invention is described in detail in the following Examples, without being limited thereby.

Example 1

After a dried chip of *Kaempferia parviflora* rhizome was ground in a mixer, 100 g of the ground matter with 1 L of 80% (v/v) ethanol added to it was subjected to 2 hours of heated reflux, then it was filtered to obtain a liquid extract. After the extract residue was subjected again to 1 hour of heated reflux in 0.8 L of 80% ethanol, it was filtered to obtain a liquid extract. The first liquid extract and the second liquid extract were put together, and subjected to depressurized concentration at 50° C., then it was dried under depression over night at 60° C. to obtain a solid of 13.3 g.

Likewise, the ground form of the dried chip of *Kaempferia parviflora* rhizome in an amount of 100 g each with one of hot water, 10% (v/v) ethanol, or 30% (v/v) ethanol in an amount of 1 L added to it was subjected to 2 hours of heated reflux, then the result was filtered to obtain a liquid extract. The respective liquid extracts were subjected to depressurized concentration at 50° C., then they were dried under depression over night at 60° C. to respectively obtain solids of 5.06 g, 5.90 g, and 7.35 g.

The 8 g of 80% ethanol extract of black ginger obtained above was partitioned a total of three times, by 100 mL of water and by 100 mL of ethyl acetate. The ethyl acetate phase was concentrated/dried, and 4.58 g of an ethyl acetate phase was obtained. The water phase was further partitioned by 100 mL of n-butanol and concentrated/dried, after which 2.45 g of a water phase and 0.92 g of a butanol phase were obtained.

Example 2

The 80% ethanol extract of black ginger obtained in Example 1 was partitioned with water and ethyl acetate and concentrated/dried, after which 4.58 g of ethyl acetate was obtained.

The obtained ethyl acetate phase was adsorbed to the silica gel, then it was eluted by a methanol-chloroform mixed solvent, and the obtained fraction was further subjected to an isolation refinement using the reversed-phase high-performance liquid chromatography (ODS) to obtain polymethoxyflavonoid Compound 1 (882 mg), Compound 2 (784 mg), Compound 3 (1224 mg), Compound 4 (463 mg) and Compound 5 (156 mg).

Structure Determination of the Compound

The chemical structure of the compounds was determined according to a common method.

Tables 2 to 6 below show the nuclear magnetic resonance spectrum of the compounds measured using the proton nuclear magnetic resonance spectroscopy ($^1$H-NMR), the carbon nuclear magnetic resonance spectroscopy ($^{13}$C-NMR). Note that the "actual measured value" in Tables 2 to 6 is a result measured by the present inventors, and the "document value" is the result described in "Simultaneous identification and quantitation of 11 flavonoid constituents in *Kaempferia parviflora* by gas chromatography. Journal of Chromatography A, 1143: 227-233, 2007."

TABLE 2

$^1$H-NMR and $^{13}$C-NMR Spectrum of Compound 1 (in CDCl$_3$)

| position | δC Actual Measured Value | δC Document Value | δH Actual Measured Value | δH Document Value |
|---|---|---|---|---|
| 2 | 162.0 | 161.9 | | |
| 3 | 109.1 | 109.0 | 6.56 (1H, s) | 6.57 (1H, s) |
| 4 | 177.6 | 177.6 | | |
| 5 | 160.8 | 160.8 | | |
| 6 | 96.0 | 96.0 | 6.34 (1H, d, J = 2.4 Hz) | 6.35 (1H, d, J = 2.4 Hz) |
| 7 | 163.9 | 163.8 | | |
| 8 | 92.8 | 92.7 | 6.53 (1H, d, J = 2.4 Hz) | 6.53 (1H, d, J = 2.4 Hz) |
| 9 | 159.8 | 159.7 | | |
| 10 | 107.6 | 107.5 | | |
| 1' | 123.8 | 123.7 | | |
| 2', 6' | 127.6 | 127.5 | 7.79 (2H, d, J = 9.0 Hz) | 7.79 (2H, d, J = 8.8 Hz) |
| 3', 5' | 114.3 | 114.2 | 6.97 (2H, d, J = 9.0 Hz) | 6.98 (2H, d, J = 8.8 Hz) |
| 4' | 160.6 | 160.6 | | |
| 5-OCH$_3$ | 56.4 | 56.4 | 3.85 (3H, s) | 3.85 (3H, s) |
| 7-OCH$_3$ | 55.7 | 55.7 | 3.88 (3H, s) | 3.90 (3H, s) |
| 4'-OCH$_3$ | 55.4 | 55.4 | 3.93 (3H, s) | 3.94 (3H, s) |

TABLE 3

$^1$H-NMR and $^{13}$C-NMR Spectrum of Compound 2 (in CDCl$_3$)

| position | δC Actual Measured Value | δC Document Value | δH Actual Measured Value | δH Document Value |
|---|---|---|---|---|
| 2 | 151.9 | 152.6 | | |
| 3 | 140.7 | 141.2 | | |
| 4 | 173.4 | 174.0 | | |
| 5 | 160.4 | 161.0 | | |
| 6 | 95.3 | 95.7 | 6.34 (1H, d, J = 2.2 Hz) | 6.33 (1H, d, J = 1.8 Hz) |
| 7 | 163.4 | 163.9 | | |
| 8 | 92.1 | 92.4 | 6.43 (1H, d, J = 2.2 Hz) | 6.49 (1H, d, J = 1.8 Hz) |
| 9 | 158.2 | 158.8 | | |
| 10 | 110.4 | 109.5 | | |
| 1' | 122.9 | 123.4 | | |
| 2' | 110.8 | 111.3 | 7.67 (1H, d, J = 2.0 Hz) | 7.73 (2H, m) |
| 6' | 121.2 | 121.6 | 7.71 (1H, dd, J = 8.4, 2.0 Hz) | |
| 3' | 148.2 | 148.7 | | |
| 4' | 150.4 | 150.8 | | |
| 5' | 110.4 | 110.8 | 6.97 (1H, d, J = 8.4 Hz) | 6.97 (1H, d, J = 8.8 Hz) |
| 3-OCH$_3$ | 59.5 | 59.9 | 3.84 (3H, s) | 3.86 (3H, s) |

TABLE 3-continued

¹H-NMR and ¹³C-NMR Spectrum of Compound 2 (in CDCl₃)

| position | δC Actual Measured Value | δC Document Value | δH Actual Measured Value | δH Document Value |
|---|---|---|---|---|
| 5-OCH₃ | 56.0 | 56.4 | 3.85 (5H, s) | 3.89 (3H, s) |
| 7-OCH₃ | 55.5 | 55.7 | | |
| 3'-OCH₃ | 55.7 | 56.0 | 3.95 (5H, s) | 3.94 (9H, s) |
| 4'-OCH₃ | 55.6 | 55.9 | | |

TABLE 4

¹H-NMR and ¹³C-NMR Spectrum of Compound 3 (in CDCl₃)

| position | δC Actual Measured Value | δC Document Value | δH Actual Measured Value | δH Document Value |
|---|---|---|---|---|
| 2 | 159.8 | 159.9 | | |
| 3 | 109.0 | 109.1 | 6.65 (1H, s) | 6.67 (1H, s) |
| 4 | 177.5 | 177.5 | | |
| 5 | 160.8 | 161.0 | | |
| 6 | 92.7 | 92.9 | 6.35 (1H, d, J = 2.4 Hz) | 6.37 (1H, d, J = 2.2 Hz) |
| 7 | 164.0 | 164.1 | | |
| 8 | 95.1 | 95.2 | 6.54 (1H, d, J = 2.4 Hz) | 6.56 (1H, d, J = 2.2 Hz) |
| 9 | 160.5 | 160.7 | | |
| 10 | 109.2 | 109.4 | | |
| 1' | 131.5 | 131.6 | | |
| 2', 6' | 125.8 | 125.9 | 7.82-7.86 (2H, m) | 7.86 (2H, m) |
| 3', 5' | 128.9 | 128.9 | 7.46-7.48 (3H, m) | 7.49 (3H, m) |
| 4' | 131.1 | 131.1 | | |
| 5-OCH₃ | 56.4 | 56.3 | 3.88 (3H, s) | 3.90 (3H, s) |
| 7-OCH₃ | 55.7 | 55.7 | 3.93 (3H, s) | 3.94 (3H, s) |

TABLE 5

¹H-NMR and ¹³C-NMR Spectrum of Compound 4 (in CDCl₃)

| position | δC Actual Measured Value | δC Document Value | δH Actual Measured Value | δH Document Value |
|---|---|---|---|---|
| 2 | 152.5 | 152.1 | | |
| 3 | 140.9 | 140.6 | | |
| 4 | 173.9 | 173.5 | | |
| 5 | 161.0 | 160.7 | | |
| 6 | 95.6 | 95.3 | 6.25 (1H, d, J = 2.2 Hz) | 6.17 (1H, d, J = 2.0 Hz) |
| 7 | 163.7 | 163.4 | | |
| 8 | 92.3 | 92.0 | 6.41 (1H, d, J = 2.2 Hz) | 6.34 (1H, d, J = 2.0 Hz) |
| 9 | 156.6 | 158.3 | | |
| 10 | 109.4 | 108.9 | | |
| 1' | 123.1 | 122.7 | | |
| 2', 6' | 129.7 | 129.3 | 7.98 (2H, d, J = 9.2 Hz) | 7.94 (2H, d, J = 9.0 Hz) |
| 3', 5' | 113.8 | 113.4 | 6.62 (2H, d, J = 9.2 Hz) | 6.87 (2H, d, J = 9.0 Hz) |
| 4' | 160.8 | 160.4 | | |
| 3-OCH₃ | 59.8 | 59.4 | 3.79 (3H, s) | 3.76 (6H, s) |
| 5-OCH₃ | 55.3 | 55.9 | 3.80 (3H, s) | |
| 7-OCH₃ | 55.7 | 55.3 | 3.81 (3H, s) | 3.82 (3H, s) |
| 4'-OCH₃ | 55.3 | 54.9 | 3.87 (3H, s) | 3.97 (3H, s) |

TABLE 6

¹H-NMR and ¹³C-NMR Spectrum of Compound 5 (in CDCl₃)

| position | δC Actual Measured Value | δC Document Value | δH Actual Measured Value | δH Document Value |
|---|---|---|---|---|
| 2 | 152.8 | 152.4 | | |
| 3 | 142.0 | 141.6 | | |
| 4 | 174.3 | 173.9 | | |
| 5 | 161.2 | 160.8 | | |

TABLE 6-continued $^1$H-NMR and $^{13}$C-NMR Spectrum of Compound 5 (in CDCl$_3$)

| position | δC Actual Measured Value | δC Document Value | δH Actual Measured Value | δH Document Value |
|---|---|---|---|---|
| 6 | 92.7 | 92.3 | 6.35 (1H, d, J = 2.4 Hz) | 6.31 (1H, d, J = 2.0 Hz) |
| 7 | 164.2 | 163.8 | | |
| 8 | 96.1 | 95.6 | 6.52 (1H, d, J = 2.4 Hz) | 6.48 (1H, d, J = 2.0 Hz) |
| 9 | 159.1 | 158.7 | | |
| 10 | 109.8 | 109.3 | | |
| 1' | 131.1 | 130.7 | | |
| 2', 6' | 128.3 | 127.9 | 8.05-8.09 (2H, m) | 8.05 (2H, m) |
| 3', 5' | 128.7 | 128.3 | 74.6-7.53 (3H, s) | 7.47 (3H, m) |
| 4' | 130.5 | 130.1 | | |
| 3-OCH$_3$ | 60.4 | 59.9 | 3.88 (3H, s) | 3.87 (3H, s) |
| 5-OCH$_3$ | 56.7 | 56.2 | 3.89 (3H, s) | 3.88 (3H, s) |
| 7-OCH$_3$ | 56.0 | 55.6 | 3.96 (3H, s) | 3.93 (3H, s) |

Further, Tables 7 to 11 below show the result of the physical property data of the compounds measured by melting point determination, infrared spectroscopy (IR), ultraviolet spectroscopy (UV) and mass spectrometry (MS).

TABLE 7

Physical Property Data of Compound 1

Yellow powder, mp: 158-161° C., IR $v_{max}$ (KBr) cm$^{-1}$: 2975, 1640, 1601, UV $\lambda_{max}$ (CHCl$_3$) nm (log ε): 229 (4.38), 266 (4.21), 319 (4.27), HREIMS m/z: 312.0994 [M]$^+$ (calcd. for C$_{18}$H$_{16}$O$_5$, 312.0998), EIMS m/z (rel. int. %): 312 (M$^+$, 100), 283 (24), 266 (22), 142 (9), 132 (11)

TABLE 8

Physical Property Data of Compound 2

Colorless powder, mp: 150-155° C., IR $v_{max}$ (KBr) cm$^{-1}$: 2970, 1625, 1605, UV $\lambda_{max}$ (CHCl$_3$) nm (log ε): 248 (4.30), 335 (4.29), HREIMS m/z: 372.1206 [M]$^+$ (calcd. for C$_{20}$H$_{20}$O$_7$, 372.1209), EIMS m/z (rel. int. %): 372 (M$^+$, 100), 357 (50), 341 (15)

TABLE 9

Physical Property Data of Compound 3

Colorless powder, mp: 149-152° C., IR $v_{max}$ (KBr) cm$^{-1}$: 2945, 1650, 1605, UV $\lambda_{max}$ (CHCl$_3$) nm (log ε): 264 (4.40), 304 (4.17), HREIMS m/z: 282.0888 [M]$^+$ (calcd. for C$_{17}$H$_{14}$O$_4$, 282.0892), EIMS m/z (rel. int. %): 2.82 (M$^+$, 100), 253 (29), 236 (25), 209 (11), 127 (8)

TABLE 10

Physical Property Data of Compound 4

Colorless powder, mp: 164-165° C., IR $v_{max}$ (KBr) cm$^{-1}$: 2949, 1740, 1601, UV $\lambda_{max}$ (CHCl$_3$) nm (log ε): 242 (4.26), 265 (4.38), 331 (4.40) HREIMS m/z: 342.1103 [M]$^+$ (calcd. for C$_{19}$H$_{18}$O$_6$, 342.1103), EIMS m/z (rel. int. %): 3.42 (M$^+$, 100),

TABLE 11

Physical Property Data of Compound 5

Colorless powder, mp: 203-207° C., IR $v_{max}$ (KBr) cm$^{-1}$: 2930, 1638, 1605, UV $\lambda_{max}$ (CHCl$_3$) nm (log ε): 242 (4.15), 263 (4.33), 323 (4.10), HREIMS m/z: 313.1078 [M]$^+$ (calcd. for C$_{13}$H$_{17}$O$_5$, 312.0998), EIMS m/z (rel. int. %): 312 (M$^+$, 92), 293 (27), 281 (7)

From the physical property data, such as the chemical shift value, the spectrum shape, the binding constant, the coupling state, and the comparison with the document value, and the melting point of the nuclear magnetic resonance spectrum ($^1$H-NMR and $^{13}$C-NMR) of the compounds, Compound 1 is identified as apigenin-5,7,4'-trimethylether, Compound 2 as quercetin-3,5,7,3',4'-pentamethylether, Compound 3 as chrysin dimethylether, Compound 4 as 3,5,7,4'-tetramethoxyflavone, and Compound 5 as 3,5,7-trimethoxyflavone.

Example 3

Confirmation Test of the Sirtuin Activity Acceleration Effect of Black Ginger Extract The sirtuin activity was measured according to the attached protocol using SIRT1 Activity Assay/Drug Discovery kit, Fluorescent (AK-555, BIOMOL International, Plymouth Meeting, Pa., USA [COSMO BIO CO., LTD., Tokyo]).

All measurement reagents (preserved at −80° C.) were stationed on ice until use to melt the SIRT1 enzyme (SE-239) and 5× Developer II (KI-176) moderately. SIRT1 enzyme was diluted to 0.2 U/μL with an assay buffer (KI-286). Resveratrol and extracts and fragments of the black ginger obtained above were used as subject samples. Solutions of 500 μg/mL were prepared using purified water for hot water extracts and the water phase fraction, and using DMSO for other samples. A solution of 10 μL/well was used for each obtained subject sample. To the control was added either DMSO or purified water instead of a subject sample. The substrate Fluor de Lys-SIRT1 (KI-177; 5 mM) plus a coenzyme NAD$^+$ (KI-282; 50 mM) were diluted with an assay buffer (KI-286) to obtain a concentration that is 3.33 folds that of the final usage concentration, and used in an amount of 15 μL/well. The subject samples (10 μL/well), SIRT1 enzyme solution (0.2 U/μL, 5 μL/well) and an assay buffer (10 μL/well) were added to the measurement microplates, and pre-incubated at 37° C. for 5 minutes. The substrate solution that was preserved preliminary at 37° C. was added at 25 μL/well, then, incubated at 37° C. for 10 minutes. Then, a reaction stop solution Developer II/2 mM nicotinamide was added at 50 μL/well, and the fluorescent probe generated from Developer II was measured (excited wave length 380 nm, fluorescent wave length 460 nm) by a fluorescent plate reader (Tecan Co., Infinite 200) within 60 minutes after the reaction stopped.

Test Result

Figure 2:
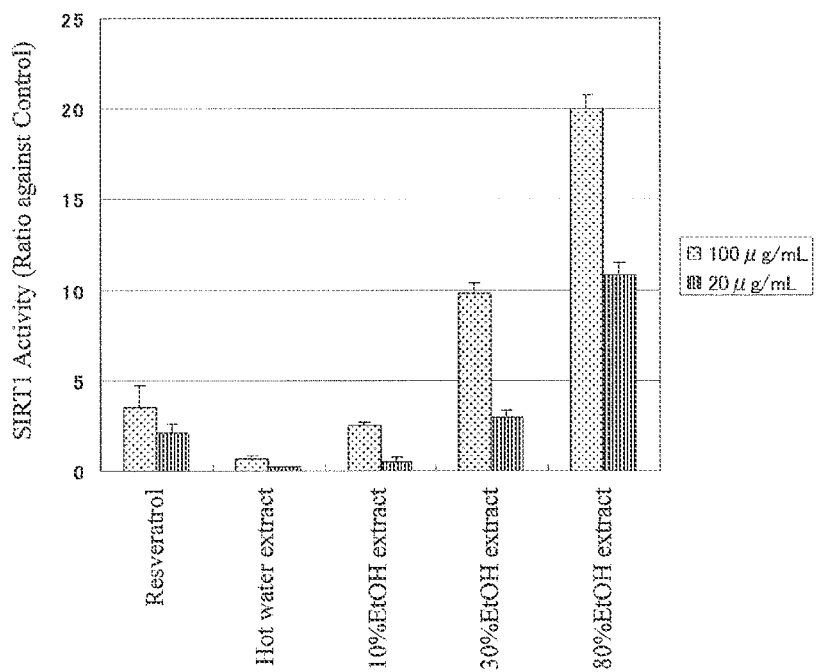
FIG. 2 is a diagram showing a result of studying the sirtuin activation effect of an extract derived from each water-containing ethanol solvent in Example 3.

The results of sirtuin activation effects of the hot water extract, the 10% ethanol extract, the 30% ethanol extract and the 80% ethanol extract of black ginger are shown in FIGS. 1 and 2. By comparison with the control value, it can be seen that the sirtuin activity was enhanced for those cases in which resveratrol, the 10% ethanol extract, the 30% ethanol extract, the 80% ethanol extract, the butanol phase fraction and the acetate ethyl phase fraction were added. In FIG. 1, the sirtuin activation by the 80% ethanol extract of black ginger and the acetate ethyl phase fraction thereof were 10 folds the activity of resveratrol or higher. Further, in FIG. 2, the sirtuin activation by the 30% ethanol extract and the 80% ethanol extract was 2 to 5 folds the activity of resveratrol or higher.

Figure 3:
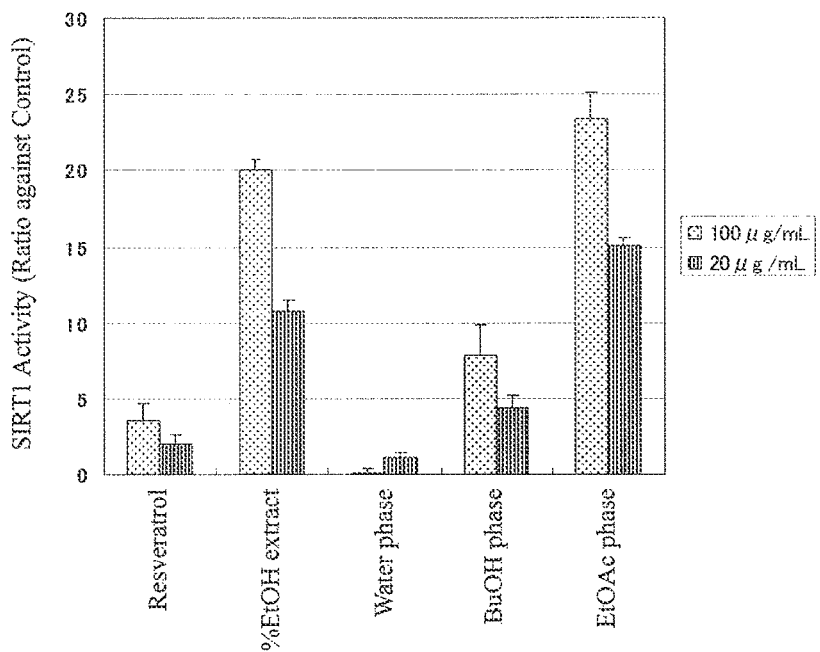
FIG. 3 is a diagram showing a result of studying the sirtuin activation effect of an 80% EtOH extract and its fractions in Example 3.

The 80% ethanol extract having the highest activity was subjected to solvent partitioning to obtain a water phase, a butanol phase and an ethyl acetate phase, and the result of measuring the sirtuin activity of the phases was that the butanol phase and the ethyl acetate phase exhibited sirtuin activity effect. In FIG. 3, the sirtuin activity effect of the ethyl acetate was 7 folds that of resveratrol.

Example 4

Confirmation Test of Metabolic Syndrome Preventative Effect of Black Ginger Extract The metabolic syndrome preventative effect of the above black ginger 80% ethanol extract was confirmed using a TSOD mouse. The TSOD mouse is an offal fat accumulative obese mouse of a multifactorial inheritance type, and it exhibits different metabolic syndrome symptoms including diabetes.

The black ginger 80% ethanol extract was mixed in a normal feed at a rate of 1.5%, and the TSOD mouse was allowed to freely intake the feed for a month. A measurement of body weight was performed over time, and a measurement of offal fat around the intestinal tract as well as a glucose tolerance test was performed when the test completed.

Test Result

Figure 4:
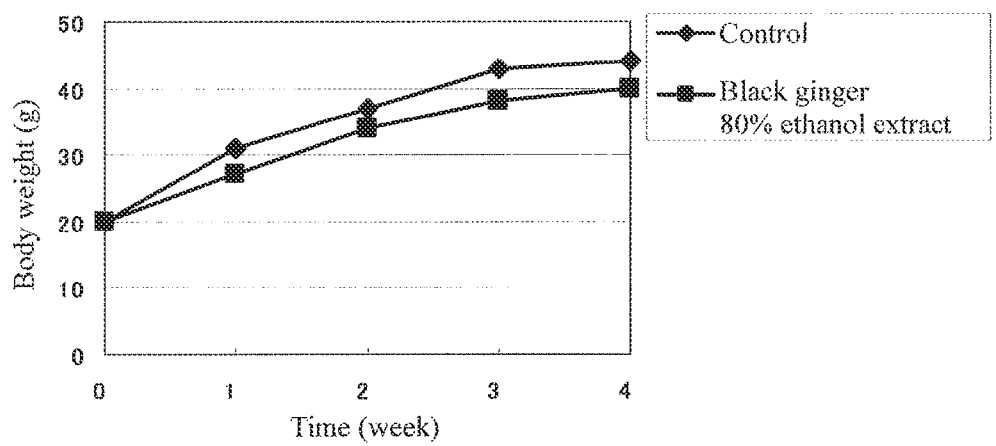
FIG. 4 is a diagram showing a result of studying the weight increase regulation effect by an animal test in Example 4.
Figure 5:
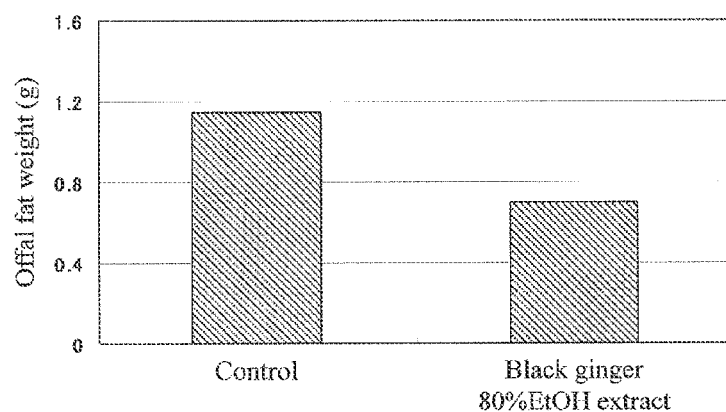
FIG. 5 is a diagram showing a result of studying an offal fat regulation effect by an animal test in Example 4
Figure 6:
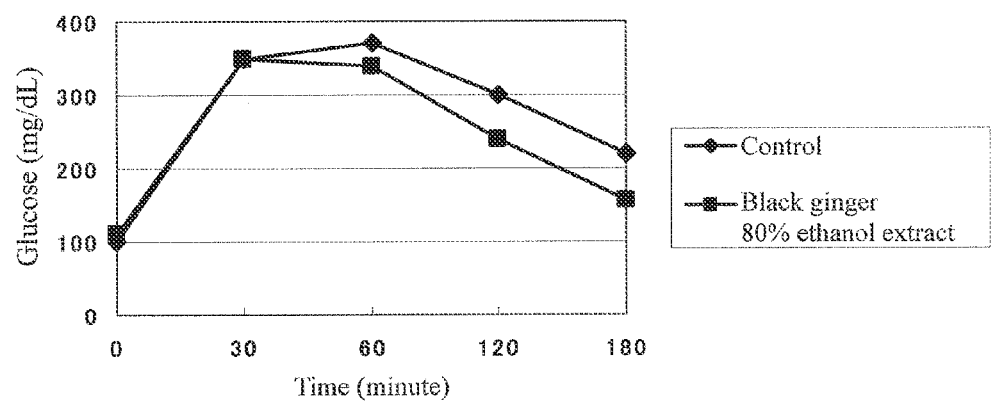
FIG. 6 is a diagram showing a result of studying the glucose tolerance improving effect by an animal test in Example 4.

The results are shown in FIGS. 4, 5 and 6. An intake of black ginger 80% ethanol extract resulted in a regulation of increase in body weight and storage of offal fat compared to the control. Further, the glucose tolerance test exhibited an improvement in the glucose tolerance abnormally.

Example 5

Confirmation Test of the Life-Lengthening Effect of Black Ginger Extract

The life-lengthening effect of the above black ginger 80% ethanol extract was studied using yeast. The budding yeast grows by budding, and the number of daughter cells that bud from one parent cell can be counted to measure the replicative lifespan of the parent cell. The present test was performed by culturing the yeast K6001 in the YPGalactose culture (2% galactose, 1% yeast extract, 2% peptone) until the logarithmic phase, washing it twice in water, and separating the yeast cells one by one using a micromanipulator. The separated parent yeast was grafted to a YPGalactose culture (2% glucose, 1% yeast extract, 2% peptone) containing the black ginger 80% ethanol extract obtained above, and cultured at 28° C. for two days, then the number of daughter cells was counted using a microscope.

Test Result

Figure 7:
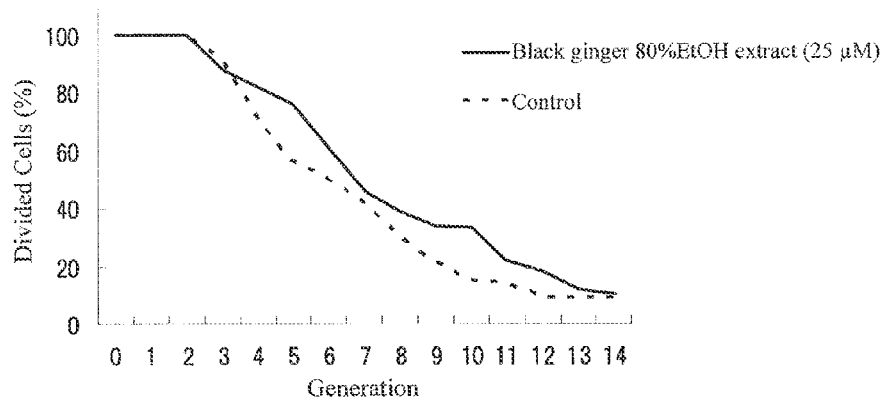
FIG. 7 is a diagram showing a result of studying the life-lengthening effect in yeast in Example 5.

The result is shown in FIG. 7. When 25 µM of a black ginger 80% ethanol extract was introduced into the culture, the number of daughter yeast increased and the replicative life-lengthening effect appeared in the yeast.

Example 6

Confirmation Test of the Sirtuin Activity Acceleration Effect of Polyalkoxyflavonoid Compounds The sirtuin activity was measured according to a protocol similar to that of Example 3.

All measurement reagents (preserved at −80° C.) were stationed on ice until use to melt the SIRT1 enzyme (SE-239) and 5× Developer II (KI-176) moderately. SIRT1 enzyme was diluted to 0.2 U/µL with an assay buffer (KI-286). Resveratrol, Compounds 1 to 5 and nobiletin (Funakoshi Co.) were used as subject samples. Each subject sample was formulated into solutions of 50 µg/mL and 10 µg/mL using DMSO, and each solution was used in an amount of 10 µL/well. To the control was added DMSO instead of a subject sample. The substrate Fluor de Lys-SIRT1 (KI-177; 5 mM) plus a coenzyme $NAD^+$ (KI-282; 50 mM) was diluted with an assay buffer (KI-286) to obtain a concentration that is 3.33 folds that of the final use concentration, and used in an amount of 15 µL/well. A subject sample solution (10 µL/well), SIRT1 enzyme solution (0.2 U/µL, 5 µL/well) and an assay buffer (10 µL/well) were added to the measurement microplate and pre-incubated at 37° C. for 5 minutes. The substrate solution that was heated preliminary at 37° C. was added at 25 µL/well, then, further incubated at 37° C. for 10 minutes. Then, a reaction stop solution Developer II/2 mM nicotinamide was added at 50 µL/well, and the fluorescent probe generated from Developer II was measured (excited wave length 360 nm, fluorescent wave length 460 nm) by a fluorescent plate reader (Tecan Co., Infinite 200) within 60 minutes after the reaction stopped.

Test Result

Figure 8:
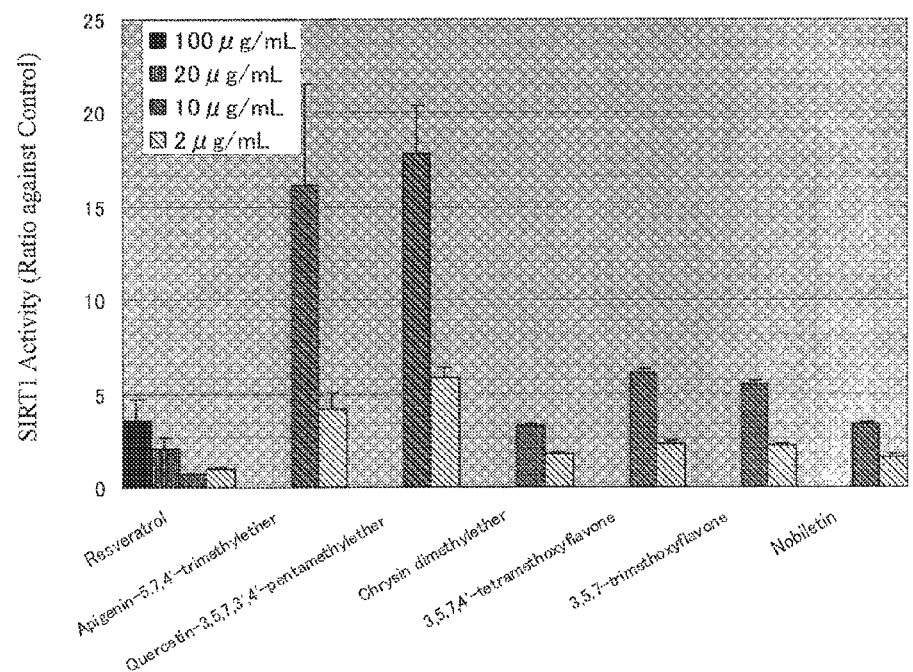
FIG. 8 is a diagram showing a result of studying the sirtuin activity acceleration effect using SIRT1 for each added subject sample in Example 6.

The result is shown in FIG. 8. The SIRT1 activity in resveratrol accelerated at concentrations of 100 µg/mL and 20 µg/mL, but almost no activity was observed at low concentrations of 10 µg/mL and 2 µg/mL. Activity was observed even at low concentrations of 10 µg/mL and 2 µg/mL for Compounds 1 to 5 and nobiletin, and Compounds 1 and 2 in particular were observed to have an extremely strong sirtuin activation activity at 10 µg/mL, 10 folds the strength of the activity of resveratrol or higher.

Prescription Example 1

Table 12 below shows a prescription example of a tablet containing the sirtuin activator of the present invention.

TABLE 12

| Component | Weight parts |
| --- | --- |
| Black ginger or black ginger extract | 10 |
| lactose | 50 |
| Starch degradation product | 40 |

Prescription Example 2

Table 13 below shows a prescription example of a soft capsule containing the sirtuin activator of the present invention.

TABLE 13

| Component | Weight parts |
| --- | --- |
| Black ginger or black ginger extract | 10 |
| lactose | 90 |

Prescription Example 3

Table 14 below shows a prescription example of a tablet candy containing the sirtuin activator of the present invention.

TABLE 14

| Component | Weight parts |
| --- | --- |
| Black ginger or black ginger extract | 10 |
| Sugar | 70 |
| glucose | 20 |

Prescription Example 4

Table 15 below shows a prescription example of a hard capsule containing the sirtuin activator of the present invention.

TABLE 15

| Component | Weight parts |
| --- | --- |
| Black ginger or black ginger extract | 10 |
| Starch degradation product | 85 |
| glycerine fatty acid ester | 3 |
| silicon dioxide | 2 |

Prescription Example 5

Table 16 below shows a prescription example of a beauty mask containing the sirtuin activator of the present invention.

TABLE 16

| Component | Weight parts |
| --- | --- |
| (Phase A) | |
| Dipropylene glycol | 5.0 |
| Polyoxyethylene (60 moles) hydro-genated castor oil | 5.0 |
| (Phase B) | |
| jojoba oil | 5.0 |
| tocopherol acetate | 0.2 |
| ethylparaben | 0.2 |
| perfume | 0.2 |
| (Phase C) | |
| sodium acid bisulfite | 0.03 |
| Polyvinyl alcohol | 13.0 |
| Black ginger or black ginger extract (1% solution) | 25.0 |
| Ethanol | 7.0 |
| Purified water | residue |

Prescription Example 6

Table 17 below shows a prescription example of a tablet containing the sirtuin activator of the present invention.

TABLE 17

| Component | Weight parts |
| --- | --- |
| Compound 1 or Compound 2 | 1 |
| Lactose | 50 |
| Crystalline cellulose | 40 |
| Starch degradation product | 9 |

Prescription Example 7

Table 18 below shows a prescription example of a soft capsule containing the sirtuin activator of the present invention.

TABLE 18

| Component | Weight parts |
| --- | --- |
| Compound 1 or Compound 2 | 1 |
| Lactose | 99 |

Prescription Example 8

Table 19 below shows a prescription example of a tablet candy containing the sirtuin activator of the present invention.

TABLE 19

| Component | Weight parts |
| --- | --- |
| Compound 1 or Compound 2 | 1 |
| Sugar | 80 |
| Glucose | 19 |

Prescription Example 9

Table 20 below shows a prescription example of a soft drink containing the sirtuin activator of the present invention.

TABLE 20

| Component | Weight parts |
| --- | --- |
| Compound 1 or Compound 2 | 1 |
| Fructose glucose liquid sugar | 50 |
| Lactose | 1 |
| Perfume | Appropriate amount |
| Purified water | residue |

INDUSTRIAL APPLICABILITY

The present invention is a sirtuin activator that shows an activation effect against the sirtuin gene relating to the aging of human and that is quite useful in preventing and treating aging, metabolic syndrome, diabetes, cancer, cardiovascular disease, and inflammation. Further, since black ginger has been eaten daily from old in countries such as Thai and Laos, it can be used widely as an extremely safe, naturally-derived sirtuin activator in various forms, such as tablets, capsules, and tablet candies. Further, the polyalkoxyflavonoid compounds can be used as medicines and health foods, and they can be used widely in various forms, such as tablets, capsules, and tablet candies.

The invention claimed is:

1. A method for treating metabolic syndrome in a subject comprising the steps of:
administering to the subject a pharmacologically effective amount of an extract of *Kaempferia parviflora* containing at least one of apigenin-5, 7, 4'-trimethylether and quercetin-3, 5, 7, 3', 4'-pentamethylether, said extract being obtained by an extraction process in which a first solvent which contains aqueous ethanol having an ethanol content of 30% to 95% (v/v) is used in a first extraction step, and a drying process in which at least one of decompression drying, freeze drying, and spray drying is used.

2. The method of claim 1, wherein said extraction process comprises a subsequent extraction step in which a different solvent which contains at least one of water, butanol, ethyl acetate, and mixtures thereof is used.

3. The method of claim 2, wherein the different solvent is ethyl acetate.

4. A method for activating sirtuin in a subject, comprising the steps of:
   administering to the subject a pharmacologically effective amount of an extract of *Kaempferia parviflora* containing at least one of apigenin-5, 7, 4'-trimethylether and quercetin-3, 5, 7, 3', 4'-pentamethylether, said extract being obtained by an extraction process in which a first solvent which contains aqueous ethanol having an ethanol content of 30% to 95% (v/v) is used in a first extraction step, and a drying process in which at least one of decompression drying, freeze drying, and spray drying is used.

5. The method of claim 4, wherein said extraction process comprises a subsequent extraction step in which a different solvent which contains at least one of water, butanol, ethyl acetate, and mixtures thereof is used.

6. The method of claim 5, wherein the different solvent is ethyl acetate.

\* \* \* \* \*